United States Patent [19]
Metcalf et al.

[11] 3,941,842
[45] Mar. 2, 1976

[54] P,P'-DISUBSTITUTED α-TRICHLOROMETHYLBENZYLANILINES
[75] Inventors: Robert L. Metcalf; Inder Kapoor; Asha Hirwe, all of Urbana, Ill.
[73] Assignee: The University of Illinois Foundation, Urbana, Ill.
[22] Filed: Dec. 26, 1972
[21] Appl. No.: 318,085

[52] U.S. Cl.... 260/570.5 R; 260/340.5; 260/521 R; 260/566 D; 260/566 F; 260/570.8 R; 260/575; 260/592; 424/282; 424/330
[51] Int. Cl.² ......................................... C07C 87/29
[58] Field of Search.... 260/570.8 R, 570.9, 570.5 R

[56] References Cited
OTHER PUBLICATIONS

Lukasiewicz, "Tetrahedron," Vol. 20, pp. 1–12 (1964).

*Primary Examiner*—Robert V. Hines
*Attorney, Agent, or Firm*—Merriam, Marshall, Shapiro & Klose

[57] ABSTRACT p,p'-disubstituted α-trichloromethylbenzylanilines are a new class of compounds which show varying degrees of utility as selective or nonselective biodegradable insecticides and/or larvicides.

17 Claims, No Drawings

P,P'-DISUBSTITUTED α-TRICHLOROMETHYLBENZYLANILINES

SUMMARY OF THE INVENTION

The present invention relates to new compositions of matter. In particular, it concerns p,p'-disubstituted α-trichloromethylbenzylanilines some of which exhibit selective or nonselective insecticidal and/or larvicidal properties, as well as greater or lesser degrees of biodegradability.

BACKGROUND OF THE INVENTION

The p,p'-disubstituted α-trichloromethylbenzylaniline compounds of the present invention are a novel class of compounds. Their properties are such that they exhibit utilities as selective or nonselective insecticides and/or larvicides. In addition, many of the members of the class of compounds of the present invention also exhibit properties of biodegradability. In view of the fact that DDT [1,1,1 trichloro-2,2-bis(p-chlorophenyl)ethane], the insecticide in most widespread use today, is not biodegradable, these latter properties take on added importance by serving to minimize one of the greatest deficiencies of prior art insecticides.

There is growing concern about the continuing liberation of vast quantities of DDT into the environment. The very qualities which make DDT such an effective contact or residual insecticide, i.e., its very low water solubility and high lipid solubility, caused by the nonpolarity of the DDT molecule, result in its accumulation in the fatty or lipid tissues of animals. These properties result in ever increasing concentrations in the tissues of carnivorous animals at the upper ends of food chains. The problems associated with this magnification phenomenon are further intensified by the enzymatic metabolic conversion of DDT to the even more stable dehydrochlorination product, DDE [1,1-dichloro-2,2-bis(p-chlorophenyl) ethylene].

Drug metabolizing enzymes, known as multifunction oxidases (MFO), which play a dominant role in detoxifying insecticides in both insects and higher animals, such as birds, fish, and mammals do not function on DDT and its metabolic derivatives DDE and DDD (or TDE) [1,1-dichloro-2,2-bis(p-chlorophenyl)ethane] as substrates. This single factor accounts for their storage and accumulation in animal tissues, especially at the higher ends of food chains.

Certain known symmetrical DDT analogs, such as methoxychlor [1,1,1-trichloro-,2,2-bis(p-methoxyphenyl)ethane] and methiochlor [1,1,1-trichloro-2,2-bis-(p-methiophenyl)ethane] are readily attacked by MFO enzymes, which metabolically convert or biodegrade such analogs into environmentally acceptable products which are rapidly eliminated by animals. Thus, methoxychlor is an example of a biodegradable insecticide which is not generally accumulated in animal tissues and is, thus, a more prudent choice than DDT for a variety of uses where environmental pollution is an important factor. However, methoxychlor, methiochlor, and other known symmetrical DDT analogs, e.g., methylchlor [1,1,1-trichloro-2,2-bis(p-methylphenyl)ethane] while exhibiting satisfactory insecticidal activity towards certain species of insects, exhibit considerably less insecticidal activity than DDT towards other species of insects.

One attempt to remedy the problems of the prior art is disclosed in the copending application of Metcalf et al., "Insecticidal Biodegradable Analog of DDT", Ser. No. 147,241 and now abandoned, filed May 26, 1971, and having a common assignee with the present application. These asymmetrical analogues of DDT disclosed therein have, in general, proved to be biodegradable and effective as insecticides. The compounds in accordance with the present invention, however, offer a mechanism of molecular cleavage whereby biodegradability may be increased. Also, certain species of the compounds of the present invention offer outstanding toxicity as either selective or non-selective insecticides. Compounds in accordance with the present invention are further distinguished from prior art insecticides in that they break down upon prolonged exposure to sunlight, which would prove to be beneficial in applications where persistence of the insecticide is either not necessary or undesirable.

DESCRIPTION OF THE INVENTION

It has been found from metabolic studies on insects, and mice, using a model ecosystem and the methods described in Kapoor, et al., 18(6) J. Agr., Food Chem. 1145 (1970), Metcalf et al., J. Environ. Sci. Technol. 709 (1971) and also in the copending application of Metcalf, et al., "Insecticidal Biodegradable Analogues of DDT", Ser. No. 147,241, filed May 26, 1971 and now abandoned, that certain p,p'-disubstituted α-trichloromethylbenzylanilines with various substituent groups are readily attacked by multifunction oxidase (MFO) enzymes, and thus are substantially biodegradable. Insecticidal activity studies involving both DDT resistant and regular strains of house flies, the blow fly, various types of mosquitoes and other insects have further indicated that the compounds of the present invention are effective insecticides.

The compounds of the present invention are p,p'-disubstituted α-trichloromethylbenzylanilines. The two p,p' substituent groups are preferably chosen from the group consisting of Cl, $CH_3$, $CH_3O$, $C_2H_5O$, $OCH_2O$, $N(CH_3)_2$, $O_2N$, $C_4H_9O$ and $C_6H_{11}$, which are biodegraded and metabolically converted to environmentally acceptable products by attack by MFO enzymes on the various substituents of the aryl rings to produce water-partitioning moieties. Also, further biodegradability is provided by separation of the two aryl rings to form benzoic acid and aniline derivatives by cleavage of the $-HN-CH(CCl_3)-$ bond, which is not present in DDT or its symmetrical or asymmetrical analogues. The presence of a nitrogen atom between the two aryl rings of the compounds of the invention thus increases biodegradability, while at the same time retaining toxicity to insects.

Such p,p'-disubstituted α-trichloromethylbenzylanilines may be synthesized in two steps: (a) the preparation of a Schiff's base by condensing one mol. of substituted benzaldehyde with one mol. of substituted aniline in boiling ethanol; and (b) treatment of the resulting benzylideneaniline with trichloroacetic acid in toluene by the method of A. Lukasiewicz, 20 Tetrahedron 1 (1964). The following example will illustrate the preparation of α-trichloromethyl-p-ethoxybenzyl-p-ethoxyaniline.

EXAMPLE 1

7.5 g. of p-ethoxy benzaldehyde and 6.8 g. of p-ethoxyaniline were refluxed in boiling ethanol for 30 minutes to give 4,4'-diethoxybenzylideneaniline, m.p. 148°C. 5.06 g. of the resulting Schiff's base and 3.4 g.

of trichloroacetic acid were refluxed in 50 ml. of toluene for 3 hrs. After the mixture was washed with 2N HCL and then with water, the toluene was distilled off. The residual oil was then crystallized from ethanol to give the desired product, m.p. 105°C, in 65% yield.

Nuclear magnetic resonance showed a singlet of $\alpha$-H at 4.95, a multiplet at 3.72–4.17 [$OCH_2$], and a multiplet at 1.2–1.5 [$CH_3$], thus fully confirming the structure.

Using techniques similar to those employed in Example 1, the other compositions shown in Table 1 were prepared and their structures likewise confirmed as we reported in Hirwe et al., 20(4) Agr. Food & Chem. 818 (1972).

The compounds of the present invention were tested for insecticidal activity by standard methods, and compared with the insecticidal activities of DDT and symmetrical analogs of DDT, such methoxychlor. Toxicological methods for the determination of the topical $LD_{50}$ values to adult female $S_{NAIDM}$ and $R_{SP}$ houseflies, Musca domestica L. and to Phormia regina, and $LC_{50}$ values to Culex pipiens quinquefasciatus Say, and Anopheles albimanus Weid mosquitoes were described by Metcalf el al., 44 Bull. World Health Org. 363 (1971). The methods for evaluation of metabolism by mouse liver homogenate and by female $R_{SP}$ housefly and salt-marsh caterpillar larvae Estigmene acrea Drury, were described by Kapoor et al., 18 J. Agr. Food Chem. 1145 (1970). The techniques for model eocsystem evluation were described by Metcalf et al., 5 J. Environ. Sci. Tech. 709 (1971). The results are detailed in Table II.

TABLE I

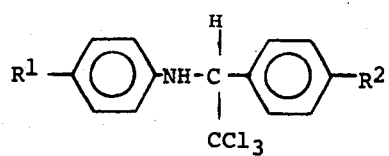

| $R^1$ | $R^2$ | Schiff's base (I) mp °C | Trichloroaminoethane (II) mp °C |
|---|---|---|---|
| Cl | Cl | 112 | 140 |
| $CH_3$ | $CH_3$ | 89 | 60 |
| $CH_3O$ | $CH_3O$ | 142 | 112 |
| $C_2H_5O$ | $C_2H_5O$ | 148 | 105 |
| $C_2H_5O$ | $CH_3O$ | 124 | 105 |
| $CH_3O$ | $CH_3$ | 82 | 60 |
| $CH_3O$ | Cl | 120 | 80 |
| Cl | $OCH_3$ | 90 | 98 |
| $CH_3$ | $C_2H_5O$ | 90 | 62 |
| $C_2H_5O$ | $CH_3$ | 110 | 84 |
| $C_2H_5O$ | Cl | 112 | 70 |
| Cl | $C_2H_5O$ | 96 | 82–83 |
| $C_2H_5O$ | $3,4\text{-}OCH_2O$ | 121 | 80 |
| $2,4\text{-}CH_3$ | $CH_3O$ | 67 | 68 |
| $3,4\text{-}CH_3$ | $CH_3O$ | 65 | 78–79 |
| $CH_3O$ | $C_4H_9O$ | 105 | 65 |
| $CH_3O$ | $N(CH_3)_2$ | 120 | 105 |
| $NO_2$ | $N(CH_3)_2$ | 230 | 175 |
| $C_2H_5O$ | H | 69 | 75 |
| $C_2H_5O$ | $2\text{-}C_2H_5O$ | 60 | 90 |
| $C_2H_5O$ | $C_2H_5O$ | 75 | 90 |
| $C_2H_5O$ | $2,4\text{-}C_2H_5O$ | 105 | 85 |
| $C_2H_5O$ | OH | 220 | 134–135 |
| OH | $C_2H_5O$ | 180 | 110 |

TABLE II

| Code | Substituents | | | Topical $LD_{50}$ μg per g for Musca domestica | | | | |
|---|---|---|---|---|---|---|---|---|
| | | | | Snaidm | | | Rsp | |
| | $R^1$ | $R^2$ | Alone | with pb | SR | Alone | with pb | SR |
| I | Cl | Cl | 115 | 13.5 | 8.5 | 220 | 25 | 8.8 |
| II | $CH_3O$ | $CH_3O$ | >500 | 5.5 | >100 | 500 | 13.5 | >37 |
| III | $C_2H_5O$ | $C_2H_5O$ | 15.5 | 4.2 | 3.7 | 20.5 | 6.5 | 3.2 |
| IV | $CH_3$ | $CH_3$ | 43.0 | 5.0 | 8.6 | 43.0 | 6.5 | 6.6 |
| V | Cl | $CH_3O$ | 23.0 | 10.5 | 2.2 | 35.5 | 12.0 | 3.0 |
| VI | $CH_3O$ | Cl | 39.0 | 6.5 | 6.0 | 49.0 | 14.0 | 3.4 |
| VII | Cl | $C_2H_5O$ | 19.0 | 10.5 | 1.8 | 31.0 | 13.5 | 2.3 |
| VIII | $C_2H_5O$ | Cl | 19.5 | 4.1 | 4.8 | 45.0 | 13.0 | 3.5 |
| IX | $CH_3$ | $CH_3O$ | 35.0 | 8.5 | 4.1 | 50.0 | 12.0 | 4.5 |
| X | $CH_3O$ | $CH_3$ | 48.0 | 8.5 | 5.6 | 65.0 | 7.5 | 8.7 |
| XI | $CH_3$ | $C_2H_5O$ | 12.5 | 2.5 | 5.0 | 14.0 | 4.4 | 3.2 |
| XII | $C_2H_5O$ | $CH_3$ | 35.0 | 14.5 | 2.4 | 70.0 | 19.5 | 3.6 |
| XIII | $CH_3O$ | $C_2H_5O$ | 23.5 | 5.5 | 4.2 | 41.0 | 12.5 | 3.3 |
| XIV | $C_2H_5O$ | $CH_3O$ | 30.0 | 3.9 | 7.7 | 37.0 | 12.0 | 3.1 |
| XV | Cl | $CH_3$ | 90.0 | 21.0 | 4.3 | 500 ca. | 36.0 | 14 |
| XVI | $CH_3$ | Cl | 65.0 | 16 | 4.1 | 125 | 30 | 4.2 |
| XVII | $C_2H_5O$ | $3,4\text{-}OCH_2O$ | 19.5 | 3.8 | 5.1 | 35.5 | 11.0 | 3.2 |
| XVIII | $CH_3O$ | $C_4H_9O$ | 370 | 12.5 | 30 | 230 | 32.0 | 7.2 |
| XIX | $C_2H_5O$ | H | >500 | 31.0 | >16 | >500 | 120 | >4 |
| XX | $4\text{-}C_2H_5O$ | $2\text{-}C_2H_5O$ | >500 | 500 | — | >500 | >500 | — |
| XXI | $2\text{-}C_2H_5O$ | $4\text{-}C_2H_5O$ | >500 | 110 | >5 | >500 | 140 | >3.5 |
| XXII | $2\text{-}C_2H_5O$ | $2,4\text{-}C_2H_5O$ | >500 | 500 | — | >500 | 500 | — |
| XXIII | $3,4\text{-}CH_3$ | $CH_3O$ | 85.0 | 6.5 | 13.0 | 100 | 28.0 | 3.6 |
| XXIV | $2,4\text{-}CH_3$ | $CH_3O$ | 95.0 | 14.0 | 6.8 | 140 | 29.0 | 4.8 |
| XXV | $CH_3O$ | $N(CH_3)_2$ | 310 | 16.0 | 19.4 | >500 | 13.5 | >37 |
| XXVI | $O_2N$ | $N(CH_3)_2$ | >500 | 120 | >4 | >500 | 500 | — |
| XXVII | $C_6H_{11}$ | $CH_3O$ | >500 | 48 | >10 | >500 | 165 | >3 |

| Code | Substituents | | | Topical $LD_{50}$ μg per g for Phormia regina | | | $LC_{50}$ ppm | |
|---|---|---|---|---|---|---|---|---|
| | | | | | | | Culex fatigans larvae, | Anopheles albimanus larvae, |
| | $R^1$ | $R^2$ | Alone | with pb | SR | | ppm | ppm |
| I | Cl | Cl | >250 | 42.5 | >5.5 | | 0.026 | 0.090 |
| II | $CH_3O$ | $CH_3O$ | 117.5 | 35.0 | 3.4 | | >1.0 | 0.64 |
| III | $C_2H_5O$ | $C_2H_5O$ | 33.7 | 9.7 | 3.7 | | 0.19 | 0.28 |
| IV | $CH_3$ | $CH_3$ | 33.7 | 21.0 | 1.6 | | 0.18 | 0.21 |

TABLE II-continued

| Code | Substituents | | Topical LD$_{50}$ μg per g for Musca domestica | | | | | |
|---|---|---|---|---|---|---|---|---|
| | R$^1$ | R$^2$ | S$_{NAIDM}$ Alone | with pb | SR | R$_{SP}$ Alone | with pb | SR |
| V | Cl | CH$_3$O | 55.0 | 15.2 | 3.6 | 0.068 | 0.12 | |
| VI | CH$_3$O | Cl | 127.5 | 80 | 1.6 | 0.44 | 0.37 | |
| VII | Cl | C$_2$H$_5$O | 24.5 | 20.0 | 1.2 | 0.032 | 0.060 | |
| VIII | C$_2$H$_5$O | Cl | 37.5 | 13.2 | 2.8 | 0.22 | 0.26 | |
| IX | CH$_3$ | CH$_3$O | 16.5 | 11.50 | 1.4 | 0.26 | 0.28 | |
| X | CH$_3$O | CH$_3$ | 135 | 14.0 | 9.6 | 0.54 | 0.48 | |
| XI | CH$_3$ | C$_2$H$_5$O | 7.7 | 4.2 | 1.8 | 0.073 | 0.085 | |
| XII | C$_2$H$_5$O | CH$_3$ | 95.0 | 42.5 | 2.2 | 0.33 | 0.30 | |
| XIII | CH$_3$O | C$_2$H$_5$O | 22.0 | 12.5 | 1.8 | 0.42 | 0.68 | |
| XIV | C$_2$H$_5$O | CH$_3$O | 112.5 | 20.0 | 5.6 | 0.34 | 1.0 | |
| XV | Cl | CH$_3$ | 72.5 | 62.5 | 1.1 | 0.066 | 0.13 | |
| XVI | CH$_3$ | Cl | 36.25 | 25 | 1.45 | 0.18 | 0.14 | |
| XVII | C$_2$H$_5$O | 3,4-OCH$_2$O | >250 | 32.5 | >7.7 | 0.23 | 0.25 | |
| XVIII | CH$_3$O | C$_4$H$_9$O | >250 | 67.5 | >4 | 0.60 | 0.77 | |
| XIX | C$_2$H$_5$O | H | >250 | >250 | — | >1.0 | 0.61 | |
| XX | 4-C$_2$H$_5$O | 2-C$_2$H$_5$O | >250 | >250 | — | >1.0 | >1.0 | |
| XXI | 2-C$_2$H$_5$O | 4-C$_2$H$_5$O | >250 | >250 | — | >1.0 | >1.0 | |
| XXII | 2-C$_2$H$_5$O | 2,4-C$_2$H$_5$O | >250 | >250 | — | >1.0 | >1.0 | |
| XXIII | 3,4-CH$_3$ | CH$_3$O | 77.5 | 15.5 | 5.0 | 0.30 | 0.18 | |
| XXIV | 2,4-CH$_3$ | CH$_3$O | 97.5 | 25.0 | 3.9 | 0.28 | 0.080 | |
| XXV | CH$_3$O | N(CH$_3$)$_2$ | >250 | 85.0 | >3 | 0.70 | 1.0 | |
| XXVI | O$_2$N | N(CH$_3$)$_2$ | >250 | >250 | — | 0.38 | >1.0 | |
| XXVII | C$_6$H$_{11}$ | CH$_3$O | >250 | 112.5 | >2 | 1.0 | >1.0 | |

Compounds of the Present Invention are Effective Insecticides

The data of Table II indicate the insect toxicity of 27 different α-trichloromethylbenzylanilines to Musca domestica (S$_{NAIDM}$ and R$_{SP}$ strains), Phormia regina, and to Culex fatigans and Anopheles albimanus. The single most effective insecticide was compound XI (α-trichloromethyl-p-ethoxybenzyl-p-methylaniline), which had the lowest LD$_{50}$ values to both strains of housefly and to Phormia and was only slightly less effective than compounds I and VII to the mosquito larvae. This compound also had the lowest synergized LD$_{50}$ values, with piperonyl butoxide (designated as "pb" in Table II), to the test insects.

Compounds which, in these tests, were only slightly less active than compound XI included compound III (α-trichloromethyl-p-ethoxybenzyl-p-ethoxyaniline) and compound VII (α-trichloromethyl p-ethoxybenzyl-p-chloroaniline). The p,p'-dichloro-substituted compound (I) was a very effective larvicide, but was of low toxicity to adult insects. Although the p,p'-dimethoxy derivative (II) was of very low toxicity, the p,p'-dimethyl derivative (IV) was one of the more insecticidal compounds.

The order of effectiveness of symmetrical substitution was found to be C$_2$H$_5$O > CH$_3$ > Cl > CH$_3$O. Toxicity was greatly decreased in the monosubstituted compound (XIX) or by substitution in the o,p' or p,o' positions (XX, XXI). Toxicity was also substantially decreased by substitution of either the aniline or benzyl ring with C$_4$H$_9$O (XVIII), N(CH$_3$)$_2$ (XXV), O$_2$N (XXVI), or cyclohexyl (XXVII), or by 2,4-disubstitution (XXII, XXIV) or 3,4-disubstitution (XXIII).

The synergistic ratios or SR values (LD$_{50}$ alone/LD$_{50}$ synergized with piperonyl butoxide) shown in Table II indicate the role of the multifunction oxidase (MFO) in detoxifying the individual compounds. Since piperonyl butoxide serves to block the action of MFO, the synergized LD$_{50}$ values express the intrinsic toxicity of the compounds. With the detoxifying action of MFO enzymes blocked, the intrinsic toxicity of the compounds can thus be measured. For the Musca domestica S$_{NAIDM}$, the compounds with the highest intrinsic toxicity were CH$_3$O,C$_2$H$_5$(XI),C$_2$H$_5$O,OCH$_3$(XIV), C$_2$H$_5$O,Cl(VIII), and C$_2$H$_5$O, OC$_2$H$_5$(III), having synergized LD$_{50}$ values of 2.5, 3.9, 4.1 and 4.2 respectively. Compound XVII (C$_2$H$_5$O, OCH$_2$O) had a value of 3.8. Compound (XI) was also outstandingly toxic to Phormia, which is deficient in MFO, with a synergized LD$_{50}$ value of 4.2.

Compound (II) had the highest SR values for susceptible and resistant flies (100 and 37) but was substantially synergized in Phormia, indicating rapid detoxication, while the Cl, OC$_2$H$_5$ compound (VII) had the lowest SR values (1.8 and 2.3). In general, higher SR values were found with compounds having a CH$_3$O group on the ring adjacent to the —NH— linkage (VI, X). This suggests that the anilinium structure favors attack by MFO·OH radical on the positively polarized CH$_3$O.

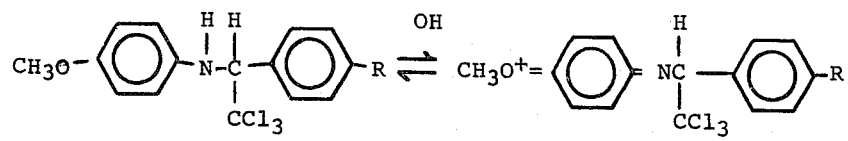

The CH$_3$O,N(CH$_3$)$_2$ compound (XXV) also had a high SR value, suggesting MFO attack by N-dealkylation.

Compounds of the Present Invention Are Biodegradable

The compound α-trichloromethyl-p-ethoxybenzyl-p-ethoxyaniline (Compound III in Table II) was selected as one of the most active insecticides for investigation of its metabolism by the adult female housefly, in the larval salt-marsh caterpillar Estigmene acrea Drury, and by mouse liver homogenate.

The biodegradability of an insecticide may be measured by administering measured doses of a tritium labeled test insecticide to a subject. Some time later the subject is sacrificed, liquefied, and a sample of the liquefied insect is placed on a thin layer chromatagraphy (tlc) plate. The plate is developed in a suitable solvent and $R_f$ values of the various compounds contained in the sample are measured against known $R_f$ values of previously synthesized theoretical metabolic breakdown products. The amount of each metabolite present may thus be measured by measuring the $^3H$ at each separately resolved spot on the tlc plate. A permanent record may be made by exposing film to the plate to form a ratioautograph.

After the amounts of the various metabolites have been calculated and a determination is made as to which of the metabolites are to be designated as "polar" and which are to be designated as "non-polar", a Biodegradability Index (amount of polar metabolites/amount of nonpolar metabolites) may be calculated. Remembering that nonpolar compounds, such as DDT are readily soluble in the fatty tissues, but are not readily soluble in water based solutions, and that the cell fluid is essentially a water based solution, the lower the Biodegradability Index, the lower the amount of biodegradability of the compound. The higher the amount of polarity, the greater the likelihood that the polar compound will dissolve in water, a very polar compound, and be eliminated from the cell.

Table III shows the metabolic breakdown products resulting from the incubation of 0.01 $\mu M$ $^3H$-labeled compound for 1 hr. with a mouse liver homogenate fortified with NADPH and nicotinamide, prepared as described by Kapoor et al., 20(1) J. Agr. Food Chem. (1970). Under these conditions the compound was attacked by O-dealkylation to produce either one or both of the monophenolic derivatives, and the compound was also cleaved at the —HN—CH(CCl$_3$)— bond to form-p-ethoxyaniline. The various amounts of the resulting metabolites are detailed in Table III.

Topical application of 1.0 $\mu g$ of $^3H$-ethoxyaniline to the prothorax of the female $R_{SP}$ housefly resulted in recovery after 24 hr. of 94.2% of the $^3H$, 10% as excreta, 65% as body homogenate, and 19.2% as body wash. The percentage of various $^3H$ metabolites in homogenate and excreta is shown in Table III.

Similar experiments were performed by feeding 0.5 mg. of $^3H$-ethoxyaniline to 4th instar salt-marsh caterpillar larvae where, after 24 hr, 75% of the $^3H$ was recovered in excreta and the remainder in the body homogenate, with the metabolic distribution also shown in Table III. These experiments in insect metabolism show results similar to those obtained with moulse liver homogenate, the results of which are also shown in Table III. Ethoxyaniline is metabolized in both the insect and the mammal by O-dealkylation to form both mono- and bis- phenols and the compound is also cleaved at the —HN—(CH(CCl$_3$)— bond to form p-ethoxyaniline and p-ethoxyphenyldichloromethylketone. Relatively large amounts of polar conjugates of the phenols were also found.

TABLE III

Metabolism of α-Trichloromethyl-p-ethoxybenzyl-p-ethoxyaniline by Housefly, Salt-Marsh Caterpillar, and Mouse Liver Homogenate

| Compound | Female housefly, percent $^3H$ in Homogenate | Female housefly, percent $^3H$ in Excreta | Salt-marsh caterpillar, percent $^3H$ in Homogenate | Salt-marsh caterpillar, percent $^3H$ in Excreta | Mouse liver percent $^3H$ in homogenate |
|---|---|---|---|---|---|
| $C_2H_5OC_6H_4NHCH(CCl_3)C_6H_4OC_2H_5$ | 37.6 | 22.9 | 9.0 | 2.5 | 30 |
| $C_2H_5OC_6H_4NHCH(CCl_3)C_6H_4OH$ or $HOC_6H_4NHCH(CCl_3)C_6H_4OC_2H_5$ | 11.5 | 25.5 | 14.4 | 4.1 | 7 |
| $HOC_6H_4NHCH(CCl_3)C_6H_4OH$ | 8.4 | 5.7 | — | — | — |
| $C_2H_5OC_6H_4C(O)CHCl_2$ | 10.4 | 9.7 | 8.7 | 3.1 | — |
| $C_2H_5OC_6H_4NH_2$ | 8.3 | 9.1 | 15.0 | 8.4 | 13.7 |
| Unknown I | 14.3 | 11.1 | 11.5 | — | 20 |
| Conjugates | 15.8 | 9.3 | 40 | 81 | 29 |

The p-ethoxydichloroacetophenone was characterized by the utilization of standard thin layer chromotography techniques. Its nmr spectrum showed $\delta(OCH_2)$ 3.72–4.17, $(CH_3)$ 1.2–1.5, (H) 6.68. Mass spectrometry showed a fragmentation pattern of a typical aromatic ketone. The peak at mass 232 was that of the basic molecule, which in turn gave rise to a fragment at m/e 149, $C_2H_5OC_6H_4C\equiv O)^+$. This base peak underwent O-dealkylation to produce the $HOC_6H_4C\equiv O^+$ ion, which fragmented further to give phenyl ion at m/e 77. Identities of α-trichloromethyl-p-hydroxyphenyl-p-hydroxyaniline, α-trichloromethyl-p-hydroxybenzyl-p-ethoxyaniline, and α-trichloromethyl-p-hydroxybenzyl-p-hydroxyaniline were confirmed by tlc cochromatography with model metabolites and by the characteristic yellow color which appeared upon exposure to ultraviolet light.

The environmental fate of any new pesticide is a factor of paramount importance in determining how and where it might be used. The behavior of $^3H$-α-trichloromethyl-p-ethoxybenzyl-p-ethoxyaniline has been studied by the model ecosystem technique following application of 5.0 mg. of labeled compound to Sorghum plants. A summary of Table IV Distribution of $^3H$-"Ethoxyaniline" and its Metabolites in a Model Ecosystem

| | Concentration (ppm) of ethoxyaniline equivalents | | | | |
|---|---|---|---|---|---|
| | $H_2O$ | Oedogonium (algae) | Physa (snail) | Culex (mosquito) | Gambusia (fish) |
| Total $^3H$ | 0.363 | 3.03 | 36.0 | 1.0 | 0.30 |
| $C_2H_5OC_6H_4NHCH(CCl_3)C_6H_4OC_2H_5$ | 0.055 | 1.09 | 22.68 | 0.28 | 0.04 |

Table IV-continued

Distribution of ³H-"Ethoxyaniline" and its Metabolites in a Model Ecosystem

| | Concentration (ppm) of ethoxyaniline equivalents | | | | |
|---|---|---|---|---|---|
| | H₂O | Oedogonium (algae) | Physa (snail) | Culex (mosquito) | Gambusia (fish) |
| C₂H₅OC₆H₄NHCH(CCl₃)C₆H₄OH | 0.031 | 0.43 | 2.02 | 0.13 | 0.08 |
| HOC₆H₄NHCH(CCl₃)C₆H₄OH | — | — | 1.512 | — | 0.03 |
| C₂H₅OC₆H₄C(O)CHCl₂ | — | 0.3 | 3.542 | — | 0.28 |
| C₂H₅OC₆H₄NH₂ | 0.053 | 0.42 | 2.556 | 0.01 | 0.03 |
| C₂H₅OC₆H₄C(O)OH | 0.123 | 0.38 | 1.800 | 0.06 | 0.03 |
| Unknown R_f 0.4 | 0.053 | — | — | 0.15 | — |
| Conjugates, polar metabolites | 0.042 | 0.40 | 2.520 | 0.22 | 0.06 | the results of these experiments are shown in Table IV. The environmental metabolites from the organisms in the model ecosystem after 33 days were identified by cochromatography with standards of known constitution, by appropriate chromogenic reagents, and by high-resolution mass spectrometry. The data of Table IV indicate the O-dealkylation of ethoxyaniline at both p-ethoxybenzyl and p-ethoxyaniline moieties to form the mono- and bis-phenols. The most interesting biological reaction is the result of dehydrochlorination to form the apparently transitory dichloroethylene intermediate which undergoes a tautomeric shift to form the dichloromethyl-p-ethoxybenzylidine-p-ethoxyaniline. The latter compound is readily hydrolyzed to p-ethoxyaniline and p-ethoxydichloroacetophenone, which subsequently forms p-ethoxybenzoic acid.

It is of interest to compare the model ecosystem behavior of compound III in Table II, α-trichloromethyl-p-ethoxy benzyl-p-ethoxy aniline, "ethoxyaniline" of Table IV, with the corresponding DDT analog "ethoxychlor" [2,2-bis(p-ethoxyphenyl)-1,1,1-trichloroethane], as evaluated by Kapoor et al., 20(1) J. Agr. Food Chem. 1 (1972). Ethoxychlor was found in the snail to 58.6 ppm and in the fish to 0.92 ppm, along with its ethylene and the mono- and bis-phenols formed by O-dealkylation. The ecological magnification (E.M.) of ethoxychlor, defined as the ratio of the parent material in the fish to the concentration in the water, was 1500-fold as compared with an E.M. of only 0.7-fold for the ethoxyaniline. It appears that both compounds are substantially biodegradable, but that the opportunity for metabolic cleavage between the , —HN—CH(CCl₃)— bond of the compounds of the present invention enhances their biodegradability.

Compounds in accordance with the present invention may be applied as an insecticide in solid form as a powder, or in solution, with or without an inert carrier.

Comparing the Biodegradability Indices (B.I.=total recovered polar metabolites/total recovered nonpolar metabolites) the values are 0.44 for ethoxychlor and 2.0 for ethoxyaniline. Although both compounds are substantially more biodegradable than DDT which, in identical experiments, was concentrated from water to fish 84,000-fold and had a Biodegradability Index of only 0.015, the compound of the present invention, ethoxyaniline, is by far superior in both E.M. and B.I.

The foregoing detailed description has been given for clearness of understanding only, and no unnecessary limitations should be understood therefrom as modifications will be obvious to those skilled in the art.

What is claimed is:

1. The compounds having the formula

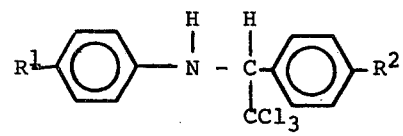

where $R^1$ and $R^2$ are selected from the group consisting of substituents Cl, CH₃, CH₃O, C₂H₅O, N(CH₃)₂, O₂N, C₄H₉O, and C₆H₁₁.

2. The compounds as defined in claim 1 wherein $R_1$ is Cl.

3. The compounds as defined in claim 1 wherein $R_1$ is CH₃.

4. The compounds as defined in claim 1 wherein $R_1$ is CH₃O.

5. The compounds as defined in claim 1 wherein $R_1$ is C₂H₅O.

6. The compounds as defined in claim 1 wherein $R_1$ is N(CH₃)₂.

7. The compounds as defined in claim 1 wherein $R_1$ is O₂N.

8. The compounds as defined in claim 1 wherein $R_1$ is C₄H₉O.

9. The compounds as defined in claim 1 wherein $R_1$ is C₆H₁₁.

10. The compounds as defined in claim 1 wherein $R_2$ is Cl.

11. The compounds as defined by claim 1 wherein $R_2$ is CH₃.

12. The compounds as defined by claim 1 wherein $R_2$ is CH₃O.

13. The compounds as defined by claim 1 wherein $R_2$ is C₂H₅O.

14. The compounds as defined by claim 1 wherein $R_2$ is N(CH₃)₂.

15. The compounds as defined by claim 1 wherein $R_2$ is O₂N.

16. The compounds as defined by claim 1 wherein $R_2$ is C₄H₉O.

17. The compounds as defined by claim 1 wherein $R_2$ is C₆H₁₁.

* * * * *